United States Patent

Mazel

Patent Number: 5,704,936
Date of Patent: Jan. 6, 1998

[54] SPINAL OSTEOSYNTHESIS DEVICE

[75] Inventor: Christian Mazel, Ville d'Avray, France

[73] Assignee: Eurosurgical, Beaurains, France

[21] Appl. No.: 318,654

[22] PCT Filed: Apr. 9, 1993

[86] PCT No.: PCT/FR93/00366

§ 371 Date: Oct. 11, 1994

§ 102(e) Date: Oct. 11, 1994

[87] PCT Pub. No.: WO93/20771

PCT Pub. Date: Oct. 28, 1993

[30] Foreign Application Priority Data

Apr. 10, 1992 [FR] France ............... 92 04449

[51] Int. Cl.⁶ ............................................. A61B 17/56
[52] U.S. Cl. .................... 606/61; 606/60; 606/69; 606/72
[58] Field of Search ................ 606/60, 61, 69, 606/70, 71, 72, 73

[56] References Cited

U.S. PATENT DOCUMENTS

| | | |
|---|---|---|
| 3,604,414 | 9/1971 | Borges .................. 606/71 |
| 4,041,939 | 8/1977 | Hall . |
| 4,047,524 | 9/1977 | Hall ...................... 606/61 |
| 5,030,220 | 7/1991 | Howland . |
| 5,053,034 | 10/1991 | Olerud ................ 606/61 |
| 5,057,109 | 10/1991 | Olerud . |
| 5,147,360 | 9/1992 | Dubousset .......... 606/61 |
| 5,300,073 | 4/1994 | Ray et al. ........... 606/61 |
| 5,417,690 | 5/1995 | Sennett et al. ...... 606/61 |

FOREIGN PATENT DOCUMENTS

| | | |
|---|---|---|
| 0 140 790 | 5/1985 | European Pat. Off. . |
| 0 301 489 | 2/1989 | European Pat. Off. . |
| 0 443 894 | 8/1991 | European Pat. Off. . |
| 2 651 992 | 3/1991 | France . |
| WO/9116018 | 10/1991 | WIPO . |

Primary Examiner—Michael Buiz
Assistant Examiner—Mark S. Leonardo
Attorney, Agent, or Firm—Young & Thompson

[57] ABSTRACT

Device including securing elements (24) with the head being expanded by an expansion screw, joining members (3, 4, 5, 6, 7) suitable for coupling to the corresponding securing elements (24), and flexible longitudinal rods (2) with a high elastic limit passing through the joining members, to which the rods can be fixed using clamps. The device is suitable for rear or front fitting.

25 Claims, 10 Drawing Sheets

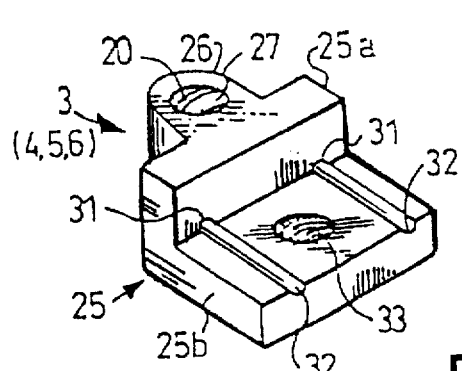
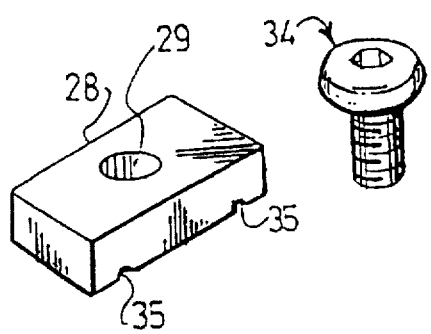
FIG. 6
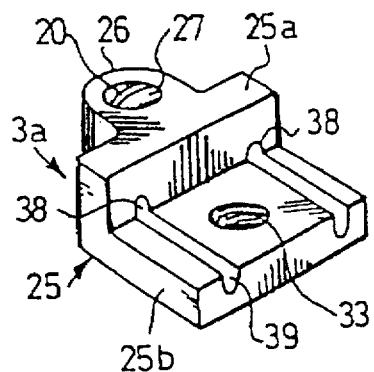
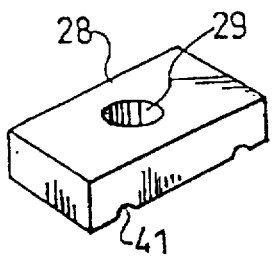
FIG. 7
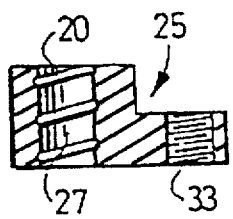
FIG. 24
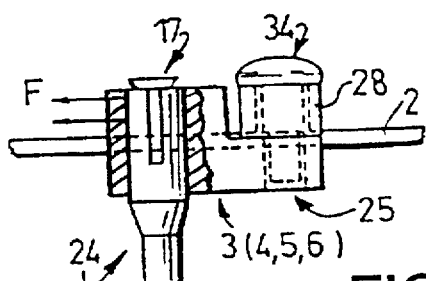
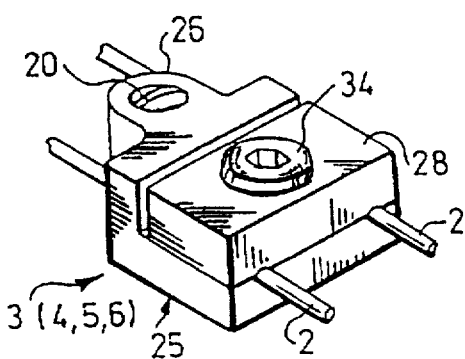
FIG. 9
FIG. 8
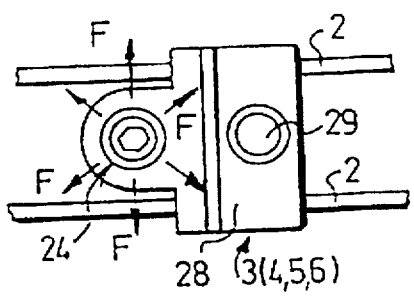
FIG. 10

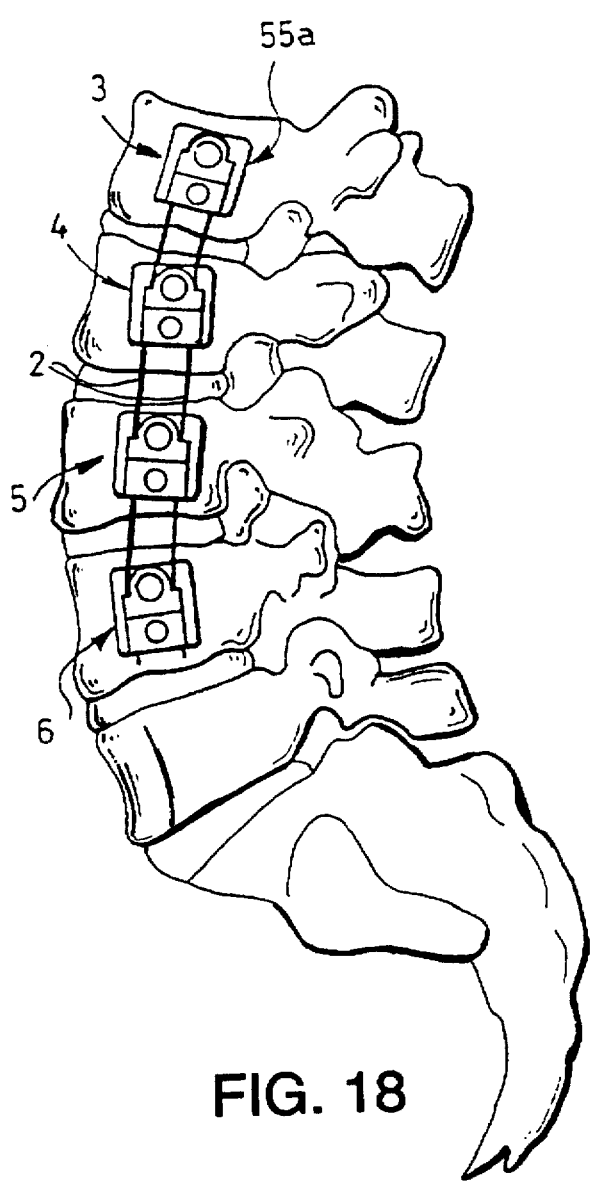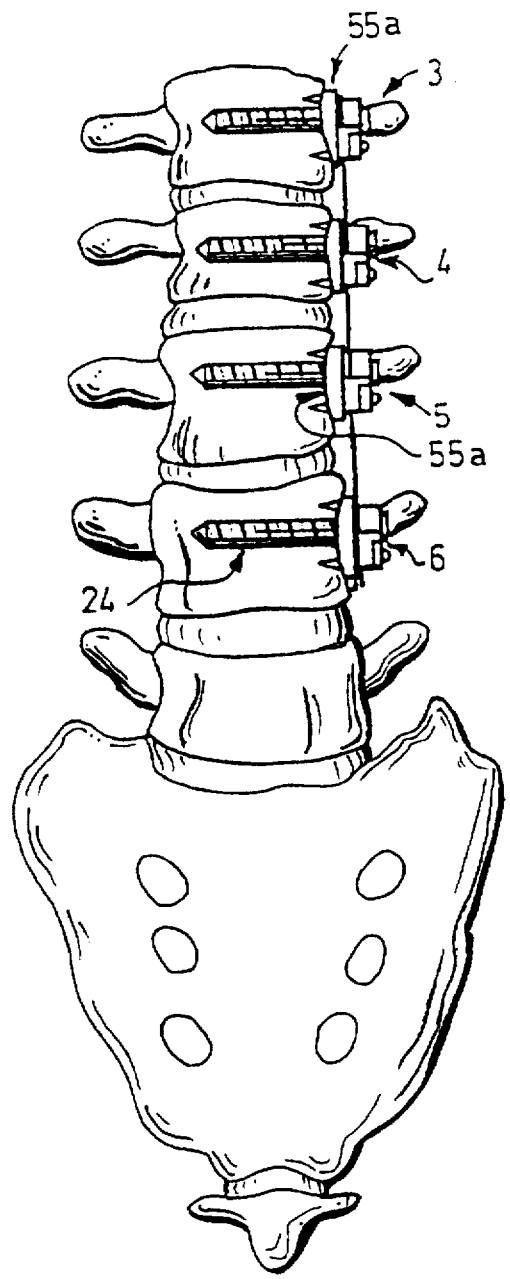
FIG. 18
FIG. 19

SPINAL OSTEOSYNTHESIS DEVICE

FIELD OF THE INVENTION

The subject of the present invention is a spinal osteosynthesis device intended for treating scolioses, tumors, fractures and degenerative pathologies.

BACKGROUND OF THE INVENTION

Spinal osteosynthesis is currently carried out principally by devices using plates or rigid rods.

By way of example, mention may be made of: Steffee plates, the WILTSE technique, the Roy Camille centipede, the CD technique, the Texas Scottish Right Hospital technique (TSRH).

These devices generally pose problems in fitting the plates or rods on the bone anchoring implants. In fact, since the positioning of these anchorings is neither straight nor has the same orientation in the sagittal plane, especially as regards vertebral screws, it is necessary to place the plates or the rods forcibly, which is prejudicial to good holding of the anchorings, or alternatively to shape the rods, for example in order to make it possible to fix the anchoring elements.

With these devices, reduction is often difficult in that it is necessary to reduce at the same time as the bone anchorings are fixed to the plates or to the rods. This reduction is difficult to carry out flexibly.

In addition, the rods or the plates must generally be curved before fitting them on the bone anchoring elements, which limits optimization of the reduction.

In the opinion of numerous surgeons, excessive rigidity of the instruments has a detrimental effect on the rapidity of bone consolidation of the graft associated with spinal osteosynthesis.

SUMMARY OF THE INVENTION

The object of the invention is to provide a segmental-fixation osteosynthesis device which can be used posteriorly, bilaterally and anteriorly, arranged so as:

to facilitate the fitting of the implants by virtue of the flexibility of the longitudinal linkages which adapt to any positioning of the anchoring elements;

to make it possible to refine the reduction by a simple movement apart or together and to rigidify the progressive mounting segment by segment;

to preserve sufficient elasticity so as to promote bone fusion of the graft associated with osteosynthesis;

to obtain instrumentation with reduced bulk.

According to the invention, the bone anchoring element for a spinal osteosynthesis device comprises a vertebral anchoring part, a cylindrical body in which are made at least two longitudinal slots, together defining at least two branches, as well as an internal screw thread, and an internal expansion screw, designed to be capable of being screwed inside the body while causing radial expansion of the branches.

The spinal osteosynthesis device according to the invention includes:

bone anchoring elements having the characteristics of the aforementioned anchoring element, connectors designed to be capable of being solidly attached to the corresponding anchoring elements, and flexible longitudinal rods with high elastic limit, passing through the connectors, means being provided for fixing these rods to the connectors.

The flexible rods are of circular or non-circular cross section, for example oblong, and are manufactured from biocompatible material with high elastic limit and high breaking strength. In addition, these flexible rods may be solid rods or alternatively assemblies of filaments such as, for example, strands.

It will be understood that such a spinal bracing device preserves a certain elasticity in the arthrodesed region, by virtue of the use of flexible metal rods with high elastic limit, which pass through a suitable number of connectors which are themselves solidly anchored to the vertebrae by elements such as screws and hooks.

The metal rods are of small cross section with respect to the rods of posterior instrumentation hitherto used, and have suitable inertia for giving the osteosynthesis the elasticity which is suitable for good bone grafting.

According to other characteristics of the invention:

each connector comprises a base in which are made two bores through which corresponding flexible rods pass, as well as a hole for receiving the expansible body of an anchoring element, and the connector also comprises means for fixing the rods to the base, the fixation means comprise a block, in one face of which channels are arranged which are complementary to corresponding channels made in one face of the base in extension of the bores, such that the flexible rods are housed in the conjugate channels of the block and of the base, the block being provided with a member for clamping on the base and for blocking the rods in their bores and channels, such as a screw passing through the smooth hole in the block and the tapped hole in the base.

BRIEF DESCRIPTION OF THE DRAWINGS

The invention will now be described with reference to the attached drawings which illustrate several embodiments thereof by way of non-limiting examples.

FIG. 6 is an exploded perspective view of the three constituent parts of a bone anchoring connector forming part of the device in FIG. 1.

FIG. 7 is a perspective view of an alternative embodiment of the connector in FIG. 6.

FIG. 8 is a perspective view of the connector in FIG. 6 assembled with two flexible rods.

FIG. 9 is a view in partial section and longitudinal elevation of the connector in FIG. 8, equipped with a bone anchoring screw.

FIG. 10 is a plan view of the connector in FIGS. 8 and 9.

3

Figure 11:
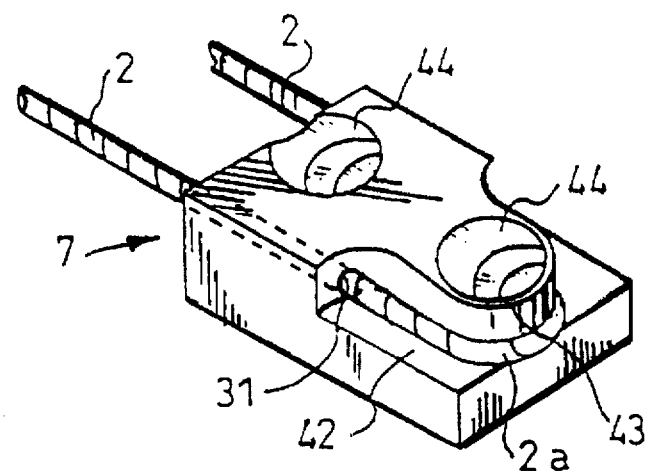
FIG. 11 is a perspective view on an enlarged scale of a sacral fixation connector forming part of the device in FIG. 1, and of the rod looped over this connector.
Figure 14:
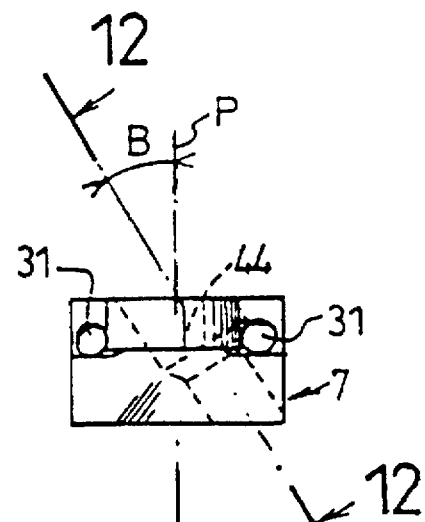
Figure 12:
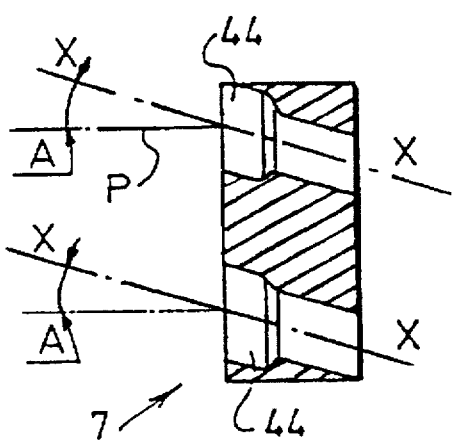

FIG. 12 is a view in longitudinal section of the connector in FIG. 11 along 12—12 in FIG. 14, in a plane containing the parallel axes, of the two bores of this connector.

Figure 13:
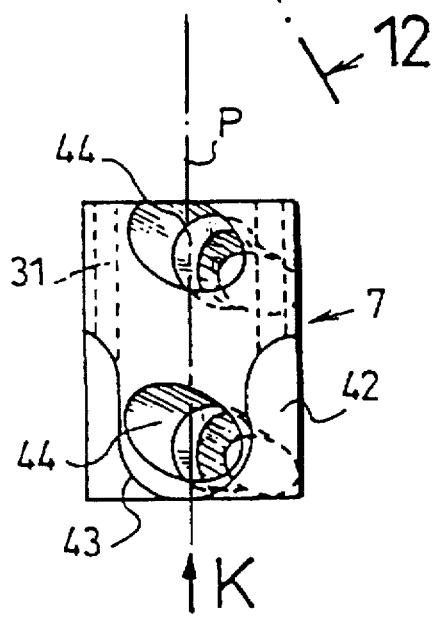

FIG. 13 is a plan view of the connector in FIG. 11.

FIG. 14 is an end view along the arrow K in FIG. 13.

Figure 15:
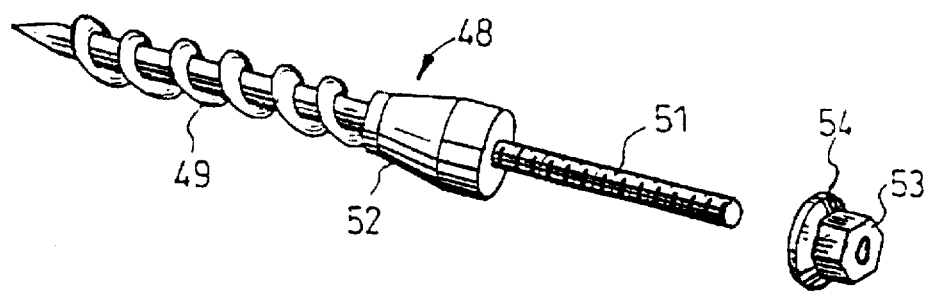

FIG. 15 is an exploded perspective view of another embodiment of the bone anchoring element.

Figure 16:
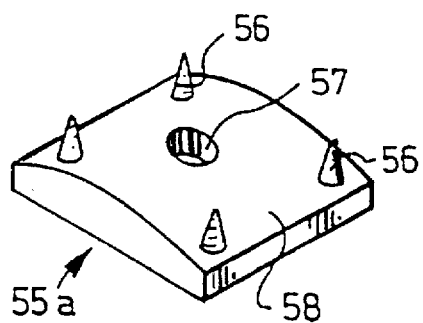
Figure 17:
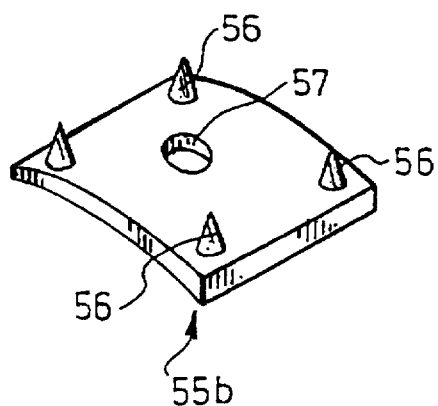

FIGS. 16 and 17 are perspective views on an enlarged scale of two embodiments of an anterior bearing plate.

FIG. 18 is a view in elevation of an anterior instrumentation including bearing plates according to the embodiment in FIG. 16.

FIG. 19 is a view in posterior elevation of the anterior instrumentation in FIG. 18.

Figure 20:
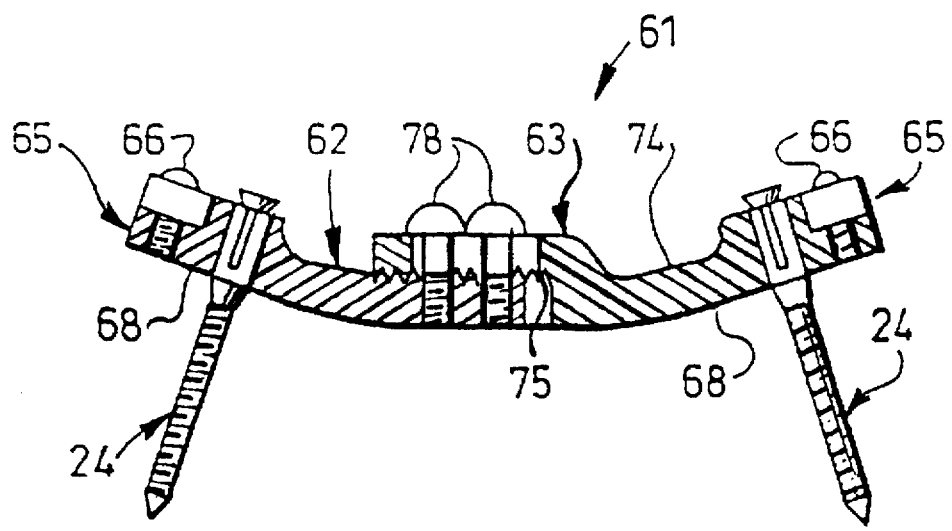

FIG. 20 is a view in longitudinal elevation of a double connector fitted with bone anchoring screws, this double connector being capable of forming a bridge above a fractured vertebra.

Figure 21:
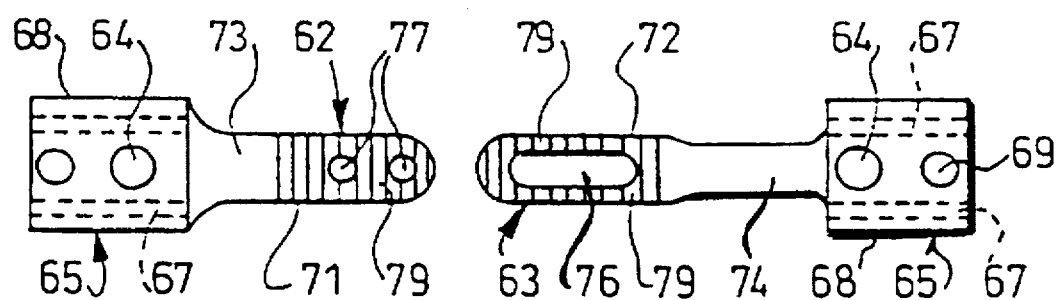

FIG. 21 is a plan view of the two constituent plates of the connector in FIG. 19.

Figure 22:
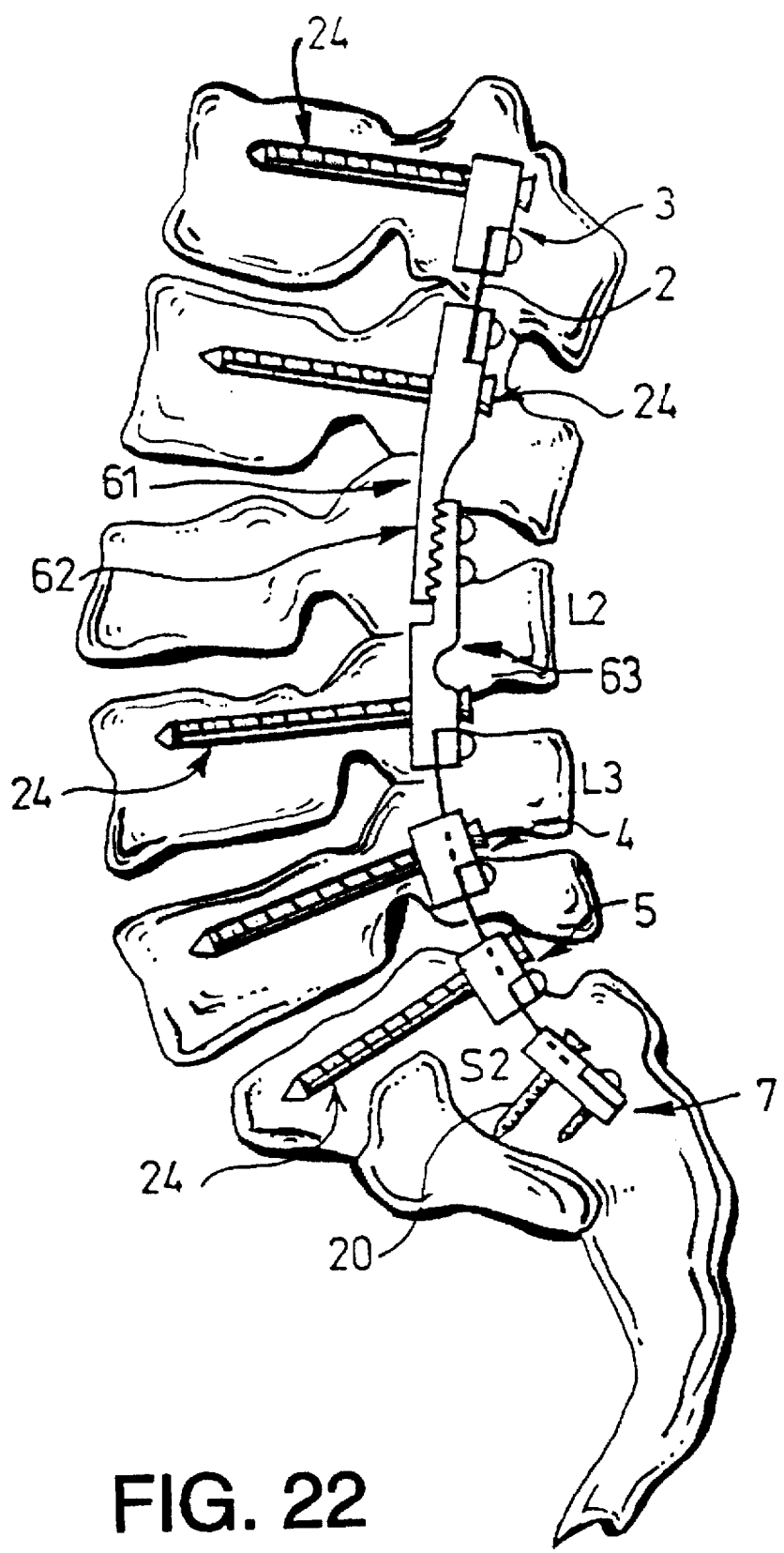

FIG. 22 is a view in side elevation of a posterior instrumentation for fractured vertebrae, fitted on the corresponding part of the spine and including a double connector according to FIGS. 20 and 21.

Figure 2:
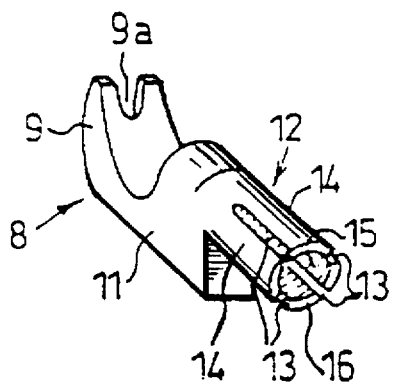
FIG. 2 is a perspective view on an enlarged scale of a bone anchoring pedical hook which can form part of the device in FIG. 1.
Figure 3:
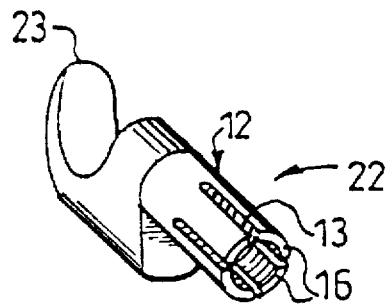
FIG. 3 is a perspective view on an enlarged scale, similar to FIG. 2, of a laminar hook and of its expansion screw.
Figure 23:
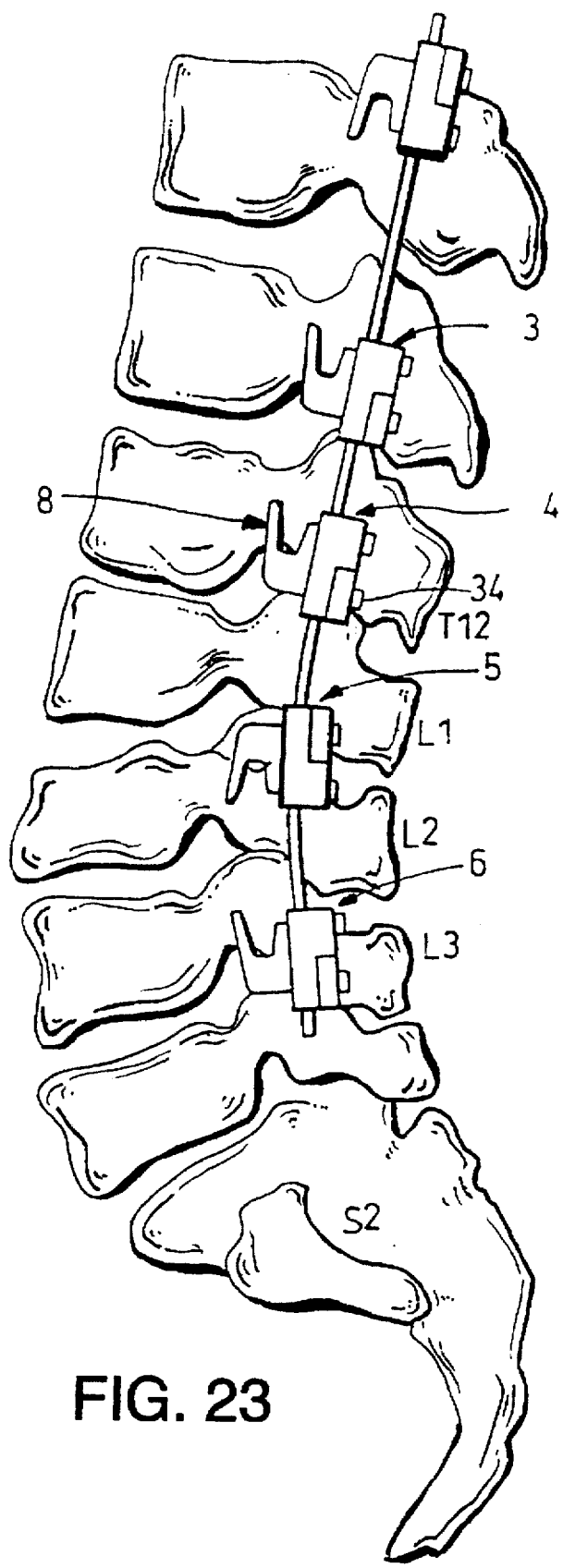

FIG. 23 is a view in sagittal elevation of a lumbar instrumentation consisting of bone anchoring elements of the pedical and laminar hook type according to FIGS. 2 and 3.

FIG. 24 is a view in partial section of the connector in FIGS. 6 to 10 at the passage hole for the bone anchoring screw.

Figure 25:
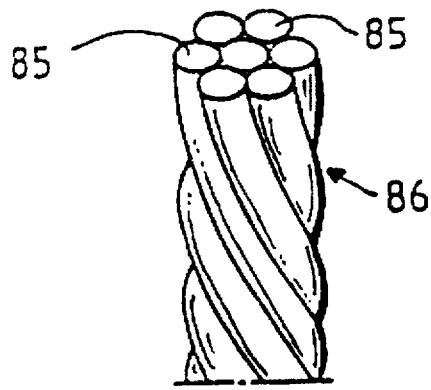

FIG. 25 is a partial perspective view on an enlarged scale of another embodiment of the flexible longitudinal rods of the device according to the invention.

Figure 26:
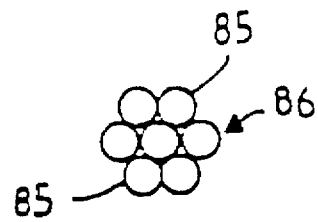

FIG. 26 is an end view of the rod in FIG. 25.

Figure 27:
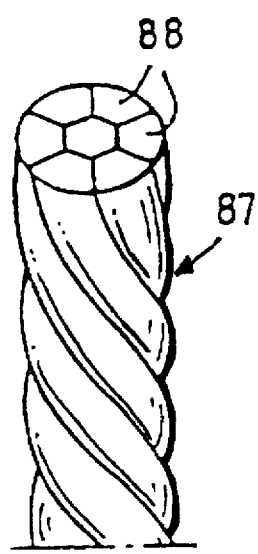

FIG. 27 is a similar view to FIG. 25 of an alternative embodiment of the flexible rod.

Figure 28:
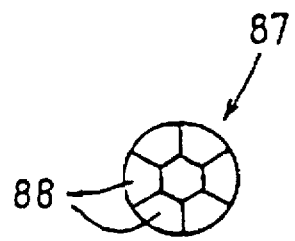

FIG. 28 is an end view of the rod in FIG. 27.

DETAILED DESCRIPTION OF THE INVENTION

Figure 1:
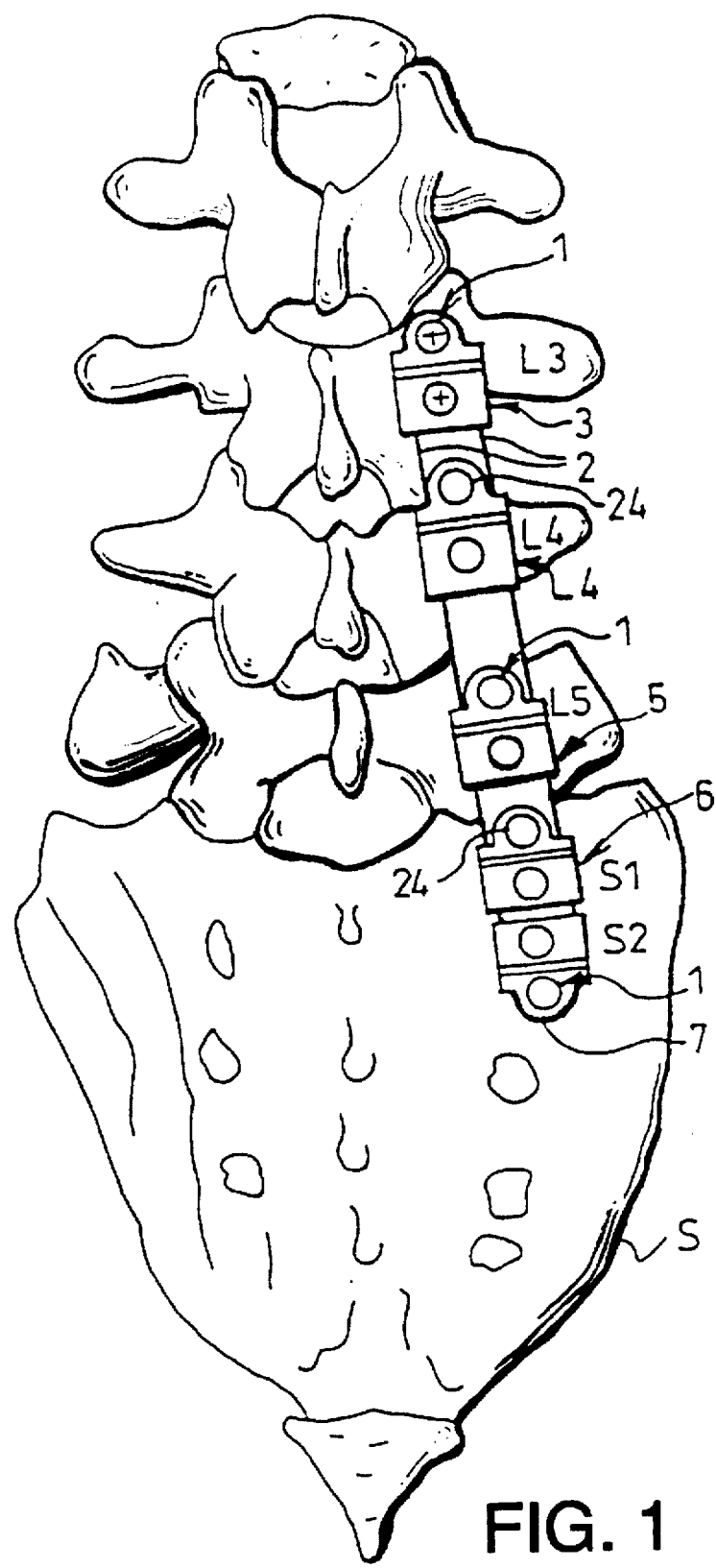
FIG. 1 is a view in elevation of a first embodiment of a spinal osteosynthesis device according to the invention, corresponding to a lumbosacral mounting.

FIG. 1 shows a spinal osteosynthesis device consisting of a lumbosacral instrumentation, extending from the sacrum S, at S1, S2 and extending over the first three lumbar vertebrae L5, L4, L3. This device comprises elements 1 for bone anchoring into the sacrum and into the lumbar vertebrae, two flexible longitudinal rods 2 with high elastic limit and small cross section, which are approximately mutually parallel and pass through the connectors (3, 4, 5, 6) to which they are fixed, and which are themselves solidly mechanically fastened to the anchoring elements 1.

In this embodiment, the two rods 2 consist of two parallel parts of a single rod bent in hairpin fashion, which pass through the first four connectors 3, 4, 5, 6, the last being anchored in the sacrum at S1. The two rods join to form a loop on a rounded portion of the sacral connector 7, placed at S2.

The rods 2 may be made of steel with high elastic limit, for example 650 N/mm², and with high breaking strength (for example 1400 N/mm²) and their diameter may be approximately 2 or 3 mm.

Description of the constituent elements of the device represented in FIG. 1 (FIGS. 2 to 14)

Figure 4:
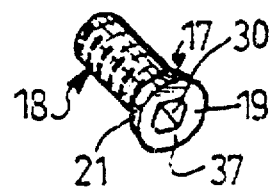
FIG. 4 is an exploded perspective view on an enlarged scale of a bone anchoring element according to a third embodiment, consisting of a pedical screw and its expansion screw.
Figure 4:
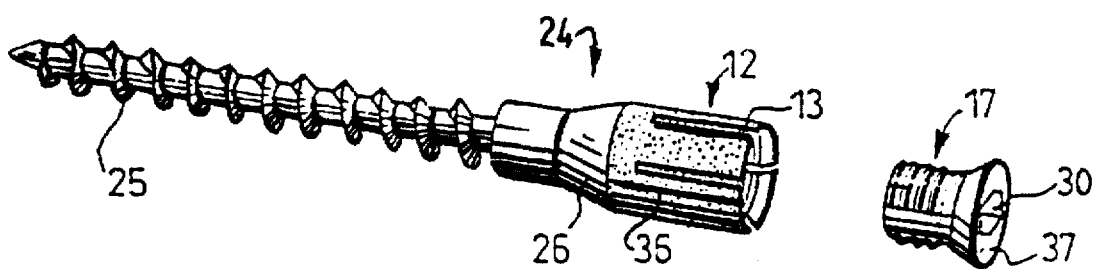
Figure 5:
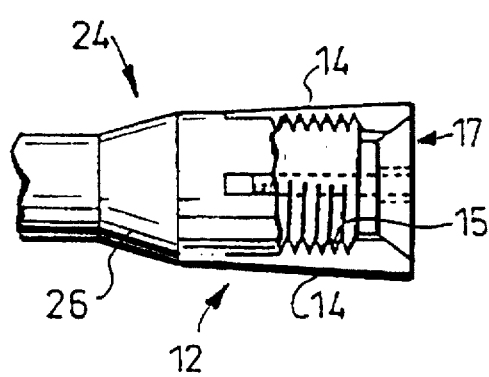
FIG. 5 is a view half in elevation and half in axial section, of the head of the screw in FIG. 4 into which the expansion screw has been inserted.

The bone anchoring elements 1 may either be hooks (FIGS. 2 and 3) or pedical screws (FIGS. 4 and 5).

4

The pedical hook 8 (FIG. 2) comprises a vertebral anchoring part consisting of the hook 9 proper, the edge of which has a notch 9a and which is connected to a mid-part 11 extended by a cylindrical body 12. At least two longitudinal slots, namely four slots 13 in the example represented, are made in this cylindrical body 12, which slots together define four radially expansible branches 14. The inner faces of these branches have an internal screw thread 15 and an annular chamfer 16 is formed on the ends of the branches 14.

Finally, the hook 8 is completed by an expansion screw 17 including a threaded rod 18 designed to be capable of being screwed into the body 12, and a head 19 provided with a conical surface 21. The latter can bear on the chamfer 16 when the screw 17 is screwed into the internal screw threads 15, causing radial expansion of the branches 14, the external surface of which then assumes a frustoconical shape.

The conical head 19 of the screw 17 has a plane surface 37 which is bordered by the conical region 21 and in which a central impression 30 is formed, designed to receive a tightening key, not shown. The impression 30 may be of both hexagonal and six-lobed shape.

The laminar hook 22 in FIG. 3 differs from the pedical hook 8 solely by virtue of its anchoring tip 23, which has a continuous edge.

The pedical screw 24 in FIGS. 4 and 5 includes a threaded bone anchoring rod 25 which is extended, on the side opposite its tip, by a conical part 26 which is itself followed by a cylindrical body 12 similar to the body 12 in FIGS. 2 and 3. At the end of screwing the associated screw 17 onto the internal screw threads 13, its conical surface 21 bears on the chamfer 16 while causing radial expansion of the branches 14 (FIG. 5).

Each of the connectors 3, 4, 5, 6 represented in FIG. 1 can be produced according to one of the two embodiments represented in FIGS. 6 to 10 and 24.

The connector 3 in FIGS. 6, 8, 9 and 10 comprises a base 25 with L-shaped profile, the short branch 25a of the L being extended by a protrusion 26 through which a tapped hole 27 is pierced. Two mutually parallel bores 31 are machined in the branch 25a, which bores pass through the branch 25a on either side of the protrusion 26. These bores 31 are circular and extend in cross section on either side of the plane of the long branch 25b of the base 25. They are extended by two semicircular parallel channels 32 which are made in the surface of the branch 25b of the L and which extend as far as the edge of the latter, through the central part of which a tapped hole 33 is pierced. The connector 3 (4, 5, 6) also includes a block 28 consisting of a small plate through which a central hole 29 is pierced and which can be placed bearing on the two branches of the L of the base 25.

The connector 3 is completed by a screw 34 whose threaded rod passes through the holes 29 and 33 when the block 28 is placed on the base 25. Two semicircular and parallel channels 35 are machined on one of the faces of the block 28 and are positioned such that, when the block 28 is placed bearing on the long branch 25b of the base 25, these channels 35 are complementary to the semicircular channels 32 in order to form circular bores in which the rods 2 can be placed.

The hole 27 is dimensioned to be capable of receiving the body 12 of the anchoring element 8, 22 or 24, a pedical screw 24 being represented engaged in the hole 27 in FIGS. 9 and 10. When the screw 17 is screwed into the body 12, the latter undergoes radial expansion (FIG. 5) and its branches 14 are strongly applied onto the wall of the hole 27, consequently solidly attaching the connector 3 and the anchoring element 8, 22 or 24. The radial expansion of the branches 14 is caused by the force exerted by the conical region 21 of the screw 17 on the chamfer 16 which has the same inclination. The outer surface of the body 12 advantageously has asperities 36 (FIG. 4) making it rough, which promotes solid attachment of the body 12 to the connector. A helicoid groove 20 is also made in the hole 27 of the connector, in order to improve the mechanical linkage between the bone anchoring element and the connector. The radial forces applied onto the walls of the protrusion 26 by tightening the screw 17 are symbolically represented by the arrows F in FIGS. 9 and 10.

The elastic flexible rods 2, once suitably positioned in the bores 31 and the channels 32, 35, can be fixed to the connector 3 by screwing the screw 34 into the holes 29 and 33 (FIGS. 8 and 9). After permanent clamping by the screw 34, the longitudinal elements 2 can slide or translate and rotate about their axis, which is advantageous when they are being fitted, because this makes it possible to adjust the gap between two bone anchorings and to twist or curve the flexible rod plus connector assembly into all the positions in order to adapt them to the anchoring elements and facilitate their introduction into the hole 27 of the connector. Once this gap has been adjusted, complete linkage between the connector 3 and the longitudinal rods 2 is provided by clamping the block 28 using the screw 34.

In the alternative embodiment in FIG. 7, the connector 3a differs from the connector 3 solely in that the bores 38 and the channels 39, 41 respectively formed on the base 25 and on the block 28 have an oblong cross section. The major axis of these oblong cross sections extends perpendicularly to the face of the branch 25b of the base 25 and to the corresponding face of the block 28. The oblong shape of the bores 38 and of the channels 39, 41 has the advantage of increasing the inertia of the corresponding oblong rods (not represented) and therefore the bending strength in the plane passing through the axis of the anchoring and parallel to the longitudinal rods.

The elements of the instrumentation described hereinabove, once assembled and fitted on a spinal segment, are, for example, as illustrated in FIG. 23.

The sacral fixation connector 7 (FIG. 11) includes, at one of its ends, a set-back part 42 defining a rounded shoulder 43, which is preferably semicircular, extended by two parallel bores 31 which pierce entirely through the connector 7. The two longitudinal rods 2 passing through the bores 31 are joined by a loop 2a which bears on the shoulder 43 and with which they therefore form a single longitudinal rod.

Two bores 44 are pierced, in the body of the connector 7, for receiving the sacral fixation screws, not represented, (such as 24). The axes XX of the bores 44 are parallel and their projections into a longitudinal axial plane (P) of the connector 7 have an inclination (A) with respect to the perpendiculars to the faces of the Connector which are contained in said plane (FIGS. 12 and 14). In addition, the axes XX have an inclination (B) with respect to the axial plane (P) (FIG. 12).

The angle A may, for example, be of the order of 15°, while B may be approximately 30°, these values being, of course, non limiting. The angle B may be oriented to the left or to the right, in order to differentiate between left sacral engagement and right sacral engagement. The bores 44 allow looping over the rounded part 43 of the flexible linkage elements 2.

The implementation and the advantages of the lumbosacral mounting illustrated in FIG. 1 are as follows.

This mounting makes it possible to stabilize and arthrodese the region of the spine consisting of the lumbar vertebrae and the sacrum, essentially S1 and S2. It is fitted using pedical screws 24, in the case of the lumbar region and the vertebra S1, and sacral screws 24 in the case of the vertebra S2. These screws constitute the bone anchorings, the sacral screws being bone-screws having a diameter of, for example, 3.5 mm, commonly used in orthopedic surgery.

The longitudinal rods 2 actually consist, as already indicated, of a single rod looped over the sacral connector 7, the two branches of the loop 2a which consist of the rods 2 then being threaded into the connectors 3, 4, 5, 6. The entire instrumentation is solidly attached to the spine by the pedical screws and sacral screws at S2. The entire device can be bent in order to make its curvature coincide with the curvature of the spine. The device is bilateral, only the right-hand side being represented in FIG. 1.

The surgical technique for fitting the device is as follows.

The screwed implants or anchorings are first fitted by the pedicals and in S1. The screws are implanted "right in front" or more laterally on the root of the transverse structure, so as to make the two pedical screws on the same vertebra converge.

The sacral fixation connector 7 and the connectors 3, 4 ... for the pedical screws and the screw of S1 are fitted on the flexible linkage elements 2. The blocks 28 are not clamped, in order to allow them to be adjusted as a function of the gaps from vertebra to vertebra, or from pedical screw to pedical screw and allow great flexibility. The assembly of flexible longitudinal elements 2 and connectors 3 ... is then bent to match the curvature of the spine (lordosis or kyphosis). Insertion is then carried out by threading the connectors over the screw heads 24.

The expansion screws 17 are tightened as the flexible rod 2/connectors 3, 4 ... assembly is introduced, the operation being carried out starting from the functional element situated uppermost on the spine, towards the sacrum. Once the assembly of connectors has been introduced and locked in the screw heads, the sacral screws of S2 are fitted in the specific sacral connector 7.

The opposite side is equipped identically. The maneuvers for reduction or correction are then carried out stage by stage, with the respective blocks being locked. This maneuver is carried out, starting from the sacrum, unilaterally or bilaterally by moving the connectors together or apart using suitable ancillary equipment. The grafts are then placed between the various spaces left by the instrumentation in order to carry out the arthrodesis.

By virtue of the fact that the heads 12 of the anchoring screws 24 have no axial end-stop, it is possible, by way of variant, to proceed as indicated hereinbelow.

In so far as the assembly comprising connectors plus flexible linkage elements 2 forms a whole, this can be fitted on the posterior face of the spine in the mariner of a spinal osteosynthesis plate. The screws 24 are then introduced through connectors left free on the flexible linkage elements 2, in order to carry out pedical anchoring. The expansion screws 17 are then fitted and screwed in in order to solidly attach the screws 24 to the connectors 3. The rest of the mounting is carried out as indicated previously.

The screw 48 represented in FIG. 15 is particularly suited to certain pathologies of the spine, such as spondylolisthesis, spondylolysis.

It has double screw-thread and therefore includes a first threaded rod 49 for bone anchoring, of the same type as the rod 25 of the pedical screws 24, and a second threaded rod 51 in the same axis as the rod 49, from which it is separated by a head 52. The rod 51 is designed to receive a nut 53, optionally provided with a widened bearing surface 54. The screw 48 is used with a connector such as 3, 4 ... or a double connector plate 61 (FIGS. 20–21) which will be described hereinbelow. After bone anchoring, screwing the nut 53 until it bears on the connector 3 ... or the plate of the double connector 61 causes displacement of the vertebra from front to back along the sagittal plane. Finally, the surgeon cuts the projecting part of the threaded rod 51.

Description of an anterior instrumentation (FIGS. 16 to 19)

Certain pathologies of the spine justify the use of instrumentation for anterior operation, called anterior instrumentation. The device according to the invention is compatible with this type of operation and fitting. However, it is then advantageously supplemented by anterior bearing plates 55a or 55b (FIGS. 16 and 17) which makes it possible to prevent the corresponding body screws 24 from being driven in (FIG. 19) and to obtain better alignment of the connectors 3, 4, 5, 6 (the device having no sacral fixation connector 7 in this use).

In fact, the vertebral body has a concavity on its periphery which sometimes makes it difficult to fit the equipment. Weak strength of the peripheral cortical also justifies widening the bearing zone on the body and avoiding direct contact of the cone 26 of the screw 24.

In order to facilitate its fitting, each bearing plate 55 is provided with conical spikes 56 which may or may not be ribbed, which position it and stabilize it until the body screw 24 is fitted. Each plate 55 is pierced with a central hole 57 for passing the body screw 24. The plate 55 is either rigid (plate 55a in FIG. 15), and thereby of sufficient thickness, with a shaped part 58 matched to the concavity of the vertebra, or flexible (plate 55b in FIG. 16) and, in this case, thinner than the plate 55a, in order to be capable of matching the concavity of the vertebra.

The other elements of the instrumentation are identical in all respects to those of the posterior instrumentation described hereinabove, apart from the fact that there is no sacral plate or engagement. The entire device, fitted on the spine, is represented in FIGS. 18 and 19.

Description of the device designed for fracture instrumentation (FIGS. 20 to 22)

The instrumentation of body fractures sometimes makes pedical screwing of the fractured vertebra or vertebrae impossible. It is therefore necessary to pass through a stage or functional vertebral element. This function is fulfilled by the double connector 61 (FIGS. 20 and 21), designed to form a bridge above a fractured vertebra.

The double connector 61 comprises two plates 62 and 63. These two plates are suitably bent in order to respect the anatomical curvature of the patient, and each include an end block 65 fitted with a clamping element (screw) 66 which makes it possible, in a manner similar to what was described hereinabove, to block the flexible rods 2 in their bores 67 which are made in the base 68 for supporting the respective blocks 65. For this purpose, these bases 68 are each pierced with a hole 69 for passing the threaded rod of the blocking screw 66, in addition to the holes 64 for passing the rods of the bone anchoring screws 24.

Each plate 62, 63 further comprises a respective elongate end part 71, 72, connected to the end base 68 by a link 73, 74. The latter has a recess 75 allowing the end 72 to be applied onto the surface of the end 71 of the plate 62. An oblong hole 76 is arranged in the end 72 and at least one hole 77 (two holes 77 in the example represented) is or are made in the elongate end 71, so that the oblong hole 76 can be placed opposite the holes 77. The two plates 62 and 63 can thus be assembled using two screws 78 passing through the oblong hole 76 and the holes 77 to block the two plates on one another (FIG. 20).

Asperities are formed on the surfaces of the plates 62, 63 which bear on each other, that is to say the elongate end surfaces 71 and 72. In the example described, these asperities consist of serrations 79 formed around the oblong hole 76 and the holes 77.

The oblong hole 76 makes it possible to adjust the relative position of the two plates 62, 63, and the asperities 79 provide the relative stability of the two plates in translation and in rotation.

The operational procedure for fitting the instrumentation including double connectors 61 (FIG. 22) is as follows.
a) Fitting the pedical screws 24 and the screw of S1.
b) Fitting the assembly consisting of the single connectors 3, 4, 5, the sacral connector 7 and a double connector 61, arranged between the connectors 3 and 4 (the connector 61 is dimensioned to straddle a fractured vertebra L2), by threading pedical screws 24 onto the bodies 12, the screws then being tightened into the connectors 3, 61, 4, 5.
c) Reduction of the fracture by maneuvering the bodies of screw 24 on either side of the fracture center.
d) Fixing and tightening the two adjustment screws 78 of the double connector 61.
e) Clamping the blocks 65 for fixing the rods 2.
f) Fitting screws 20 at S2.

The last two operations can be interchanged.

A mixed mounting is then obtained which has increased rigidity in the fracture center, by virtue of the double connector 61, and is more elastic on either side of the center, which ensures global stability of the spine.

The hooks 8 and 22 are, of course, used when this is appropriate, the mountings illustrated in the drawings being provided solely by way of example.

FIGS. 25 and 26 illustrate another embodiment of the longitudinal flexible rods, here each consisting not of a solid rod such as 2, but of an assembly of filaments 85 forming a strand 86. In this example, the strand 86 is thus produced by assembling 7 filaments 85, and may be of reduced diameter.

The rods or strands 86 should take up the tensile and compressive forces and allow some degree of flexibility for taking up the displacements imposed on them. The use of a strand or of a solid rod can improve the bending fatigue strength of the longitudinal element. In fact, the rod 86 may have a diameter of, for example, 2 mm or 2.5 mm. It is clear that a strand, for example of 7 filaments, will have reduced filament diameters, which will give it great flexibility.

In the alternative embodiment in FIGS. 27–28, the strand 87 consists of an assembly of 7 filaments 88 (one central filament and six peripheral filaments) which are redrawn in order to increase the metal cross section and the rigidity of the strand.

The strands 86, 87 may include a variable number of filaments, and be made, for example, of stainless steel 316 L with high elastic limit.

The use of solid rods 2 or of strands 86, 87 is identical. The improvement in flexibility provided by the strands may occur to the detriment of the compressive strength. In consequence, the choice of a solid rod or a strand, and its composition, is a compromise as a function of the indications.

This device can be used in posterior or anterior operation. The assembly of rods and connectors, by virtue of the flexibility of these rods, makes it possible to adapt with ease and without constraint to any positioning of the bone anchoring elements. The sliding of the connectors over the rods after fixing of the bone anchoring elements thereto makes it possible to refine the reduction of the instrumented spinal segment. Fixing the connectors onto the rods by clamping rigidifies the assembly whilst retaining some degree of elasticity for the instrumentation by virtue of the mechanical characteristics of the rods, thus promoting taking of the bone graft associated with osteosynthesis.

The vertebral screws may be introduced before the linkage elements or through them.

I claim:

1. A spinal osteosynthesis device comprising:
    bone anchoring elements, each element comprising a vertebral anchoring part, a cylindrical body having at least two longitudinal slots together defining at least two branches, said cylindrical body having an internal screw thread, said anchoring element having an internal expansion screw adapted to be screwed inside said cylindrical body while causing radial expansion of the branches,
    connectors including means for attaching said connectors to the corresponding anchoring elements, and
    flexible longitudinal rods for use on a spine of a patient, said rods passing through the connectors, means for fixing said rods to the connectors, said rods constructed and arranged to preserve the flexibility necessary for a good bone fusion, said rods having a diameter ranging from about 2 to about 3 mm, and being made of a material having a high elastic limit and a high breaking strength, and said device forming a flexible structure in use on the spine of the patient.

2. Device according to claim 1, further including a sacral connector provided with two bores with parallel axes projecting into a longitudinal axial plane of the sacral connector and forming a first inclination with respect to perpendiculars to faces of the sacral connector which are contained in said plane, and said axes forming a second inclination with respect to said axial plane.

3. Device according to claim 2, wherein the sacral connector includes a rounded shoulder having ends which merge into through bores, for passing a loop which links two rods.

4. Device according to claim 1, further including plates for anterior bearing on the spine, each plate having means for fixation on a corresponding vertebra, each plate being constructed and arranged to match the concavity of said vertebra, and each plate being pierced with a hole for passage of one of the bone anchoring element passing through the connector mounted on said plate.

5. Device according to claim 4, wherein each plate is rigid with a shaped part matched to the concavity of the associated vertebra.

6. Device according to claim 4, wherein each plate has a sufficiently small thickness to make it flexible in order to allow said plate to match said concavity.

7. Device according to claim 1, further including at least one connector means designed to form a bridge above a fractured vertebra, said connector means including two plates each pierced with a bore for passage of one of the bone anchoring elements and provided with blocks for fixing the rods, means for longitudinal adjustment of the plates with respect to one another, and means for assembling said plates together, each plate having an end part, one of the plates having a recess for allowing its end part to bear on the corresponding end part of the other of the plates.

8. Device according to claim 7, wherein said adjustment means comprise an oblong hole arranged in one of the plates, said means for assembling comprising at least one tapped hole in the other of said plates, facing the oblong hole, and an assembly screw, said plates being bent in order to match the anatomical curvature of the patient while being assembled in extension of one another.

9. Device according to claim 8, wherein asperities are formed on surfaces of the plates which bear on one another.

10. Device according to claim 1, wherein the flexible longitudinal rods have a cross-section which is one of circular and oblong.

11. Device according to claim 1, wherein the flexible longitudinal rods comprise an assembly of filaments forming a strand.

12. A spinal osteosynthesis device comprising:
    bone anchoring elements, each element comprising a vertebral anchoring part, a cylindrical body having at least two longitudinal slots together defining at least two branches, said cylindrical body having an internal screw thread, said anchoring element having an internal expansion screw adapted to be screwed inside said cylindrical body while causing radial expansion of the branches,
    flexible longitudinal rods for use on a spine of a patient, and
    connectors including means for attaching said connectors to said anchoring elements and to said longitudinal rods, each connector comprising a L-shaped base pierced entirely by two through bores and a hole for receiving said cylindrical body of an anchoring element, first channels arranged on said base and extending said through bores, said connector including a block for immobilizing said rods, said block being clamped on said base by a clamping means, said block having second channels complementary to said first channels, said rods being accommodated within said through bores and said first and second channels, said device forming a flexible structure in use on the spine of the patient.

13. Device according to claim 12, wherein the through bores and the first channels are one of circular and oblong.

14. Device according to claim 12, wherein the hole for receiving the cylindrical body in each connector includes a helicoid groove improving mechanical fixing of the anchoring elements to the connectors.

15. Device according to claim 12, further including a sacral connector provided with two bores with parallel axes projecting into longitudinal axial plane of the sacral connector and forming a first inclination with respect to perpendiculars to faces of the sacral connector which are contained in said plane, and said axes forming a second inclination with respect to said axial plane.

16. Device according to claim 15, wherein the sacral connector includes a rounded shoulder having ends which merge into the through bores, for passing a loop which links the two rods.

17. Device according to claim 12, further including plates for anterior bearing on the spine, each plate having means for fixation on a corresponding vertebra, each plate being constructed and arranged to match the concavity of said vertebra, and each plate being pierced with a hole for passage of one of the bone anchoring elements passing through the connector mounted on said plate.

18. Device according to claim 17, wherein each plate is rigid with a shaped part matched to the concavity of the associated vertebra.

19. Device according to claim 17, wherein each plate has a sufficiently small thickness to make it flexible in order to allow said plate to match said concavity.

20. Device according to claim 12, further including at least one connector means designed to form a bridge above a fractured vertebra, said connector means including two plates each pierced with a bore for passage of one of the bone anchoring element and provided with blocks for fixing the rods, means for longitudinal adjustment of the plates with respect to one another, and means for assembling said plates together, each plate having an end part, one of the plates having a recess for allowing its end part to bear on the corresponding end part of the other of the plates.

21. Device according to claim 20, wherein said adjustment means comprise an oblong hole arranged in one of the plates, said means for assembling comprising at least one tapped hole in the other of said plates, facing the oblong hole, and an assembly screw, said plates being bent in order to match the anatomical curvature of the patient while being assembled in extension of one another.

22. Device according to claim 21, wherein asperities are formed on surfaces of the plates which bear on one another.

23. Device according to claim 12, wherein the flexible longitudinal rods have a cross-section which is one of circular and oblong.

24. Device according to claim 12, wherein the flexible longitudinal rods are made of a material having a high elastic limit and a high breaking strength.

25. Device according to claim 12, wherein the flexible longitudinal rods comprise an assembly of filaments forming a strand.

* * * * *